United States Patent [19]
Lancaster et al.

[11] Patent Number: 5,863,717
[45] Date of Patent: Jan. 26, 1999

[54] USE OF CONSERVED OLIGONUCLEOTIDE PRIMERS TO AMPLIFY HUMAN PAPILLOMAVIRUS DNA SEQUENCES

[75] Inventors: Wayne D. Lancaster; Lucie Grégoire, both of Grosse Point Park, Mich.

[73] Assignee: Abbott Laboratories, Abbott Park, Ill.

[21] Appl. No.: 431,444

[22] Filed: Nov. 3, 1989

[51] Int. Cl.$^6$ .............................. C12Q 1/70; C12Q 1/68; C12P 19/34; C07H 21/02

[52] U.S. Cl. ................. 435/5; 435/6; 435/4; 435/91.1; 435/91.2; 536/23.1; 536/24.3; 536/24.33; 536/23.72; 536/26.6

[58] Field of Search ................................ 436/6, 27, 91, 436/501, 811; 935/9, 16, 17, 70, 88; 435/6, 5, 4, 91.1, 91.2; 536/23.1, 24.3, 23.72, 24.33, 26.6

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,983,728 | 1/1991 | Herzog et al. | 436/27 |
| 5,176,995 | 1/1993 | Sninsky et al. | 435/6 |
| 5,705,627 | 1/1998 | Manos et al. | 435/6 |

FOREIGN PATENT DOCUMENTS

| | | |
|---|---|---|
| 301968 | 2/1986 | European Pat. Off. . |
| 0425995 | 5/1991 | European Pat. Off. . |
| 8902934 | 4/1989 | WIPO . |

OTHER PUBLICATIONS

C. Oste, *BioTechniques*, 6, 162 (1988).
J. Campione–Piccardo et al., Abstract presented May 16–20, 1988 at Seventh International Papilloma Virus Workshop, Cote d'Azur, France vol #, page # not relevant.
A. Cravadore et al., *Molecular and Cellular Probes*, 3, 143 (1989).
Yong et al. Brit Med. J 298:14 (1989).
Shibata et al. Lab Inves. 59(4)555 (1988).
Cole et al. J. Mol Biol 193:599 (1987).
Shibata et al Can Res. 48:4564 (1988).
Melchers et al J. Med. Virol 27:329 (1989).
Fuch et al. J of Virol 58(2): 626 (1986).
Ohtsuka et al. J. Biol Chem. 260(5)2605 (1985).
Shibata et al. J. Exp. Med. 167 : 225 (1988).
Broker et al Cancer Cells 4 : 17 (1986).
Evander et al. Abs. Seventh. Int. Papillama Virus Workshop. France p. 27 (vol # not applicable) (1988).
Evander et al. Abs. 1 117 J. Cell. Bioch. Supp 13(C) (1989) page # not applicable.

*Primary Examiner*—W. Gary Jones
*Assistant Examiner*—Dianne Rees
*Attorney, Agent, or Firm*—Thomas D. Brainard; Paul D. Yasger

[57] ABSTRACT

Two oligonucleotides are provided which function as amplifying primers when used in tandem in the polymerase chain reaction with HPV DNA. The primers are of the formulae:

IU: 5'-TIIN$_1$IN$_1$IIN$_2$TAAAACGAAAGT-3' and

IWDO: 5'-N$_1$TCN$_1$N$_3$AIGCCCAN$_2$TGIACCAT-3' wherein N$_1$ is A or G, N$_2$ is C or T and N$_3$ is A or T.

13 Claims, 3 Drawing Sheets

USE OF CONSERVED OLIGONUCLEOTIDE PRIMERS TO AMPLIFY HUMAN PAPILLOMAVIRUS DNA SEQUENCES

BACKGROUND OF THE INVENTION

Infection of the anogenital track by human papillomavirus (HPV) is now recognized as a venerally-transmitted disease which often is associated with the pathogenesis of cancer and its precursor lesions. Of the more than 50 known HPV types, at least 21 infect the anogenital tract. These mucosotropic viruses are most frequently associated with benign condyloma or latent infections. However, the presence of HPV in premalignant lesions and invasive cancers, particularly of the cervix, may reflect the oncogenic potential of these viruses. See P. M. Howley, in *Important Advances in Oncology*, D. T. DeVita, Jr., et al., eds., J. B. Lippincott, Philadelphia, Pa. (1987) at pages 55–73.

Certain virus types, namely HPV 16 and 18, and to a lesser extent HPV 31, 33 and 35, are found in a high proportion of invasive cervical cancers and their metastases. However, many HPVs infecting the anogenital tract, such as HPV 6 and 11, are found most commonly in benign condyloma and only rarely in invasive cancers. Thus, HPVs detected in the anogenital tract can be broadly classified as low (HPV 6 and 11), intermediate (HPV 31, 33 and 35) or high (HPV 16 and 18) risk viruses based on their association with malignancy. A. T. Lorincz et al., *J. Natl. Cancer Inst.*, 79, 671 (1987). In a recent study, HPV 18 failed to be detected in premalignant lesions but was found in 17% of invasive cervical cancers suggesting that this virus may be associated with a rapid disease course. R. J. Kurman et al., *Am. J. Obstet. Gynecol.*, 159, 293 (1988). In addition, HPV 18 tended to be associated more frequently with higher grade tumors and metastases in younger patients than HPV 16. W. Barnes et al., *Gynecol. Oncol.*, 29, 269 (1988).

For these reasons, a need exists for methods to identify and type HPV in clinical specimens. Broadly cross-reactive polyclonal antisera prepared by immunization of animals with disrupted virions have proven capable of detecting HPV antigens in about 30–70% of cutaneous and mucosal warts. Immunological tests have two major handicaps. Only well-differentiated cells appear capable of viral antigen expression. Thus, HPV-infected tissues showing higher degrees of neoplasia, such as carcinoma in situ, rarely contain HPV antigen. Secondly, the test is not able to identify specific viral types.

Since no immunological test is currently available for virus typing, molecular hybridization techniques have been used for the detection and typing of HPV DNA and RNA in clinical specimens. See A. T. Lorinez, *Obstetrics and Gynecol. Clinics of N. Amer.*, 14, 451 (1987). Many of these techniques use labelled single-stranded DNA probes which are complementary to, and thus which can bind to, known regions of the viral genome. In Southern blotting, viral DNA is isolated from lysed cells, purified, and broken into fragments of known molecular weight by restriction enzyme digestion. The fragments are denatured and physically separated by gel electrophoresis. The single-stranded fragments are then contacted with either a mixture of labelled HPV probes, to diagnose infection, or with a panel of HPV type-specific probes. HPV fragments which react with probe can be identified by detection of the bound label.

The use of such molecular hybridization techniques to detect homologous DNA sequences are sensitive and can be highly specific if used with probes which bind to nucleic acid sequences which are unique to a particular HPV type. However, the steps required to isolate and purify the viral DNA are technically cumbersome, and the concentrations of total viral DNA in a given clinical sample may be below the limit of sensitivity of the test. For example, in dysplastic cervical lesions, the amount of viral DNA is reduced with increasing dysplasia. An in situ RNA probe has been able to detect and type HPV in cervical squamous cell carcinoma, but requires four weeks of autoradiography to detect the bound probe.

Figure 1:
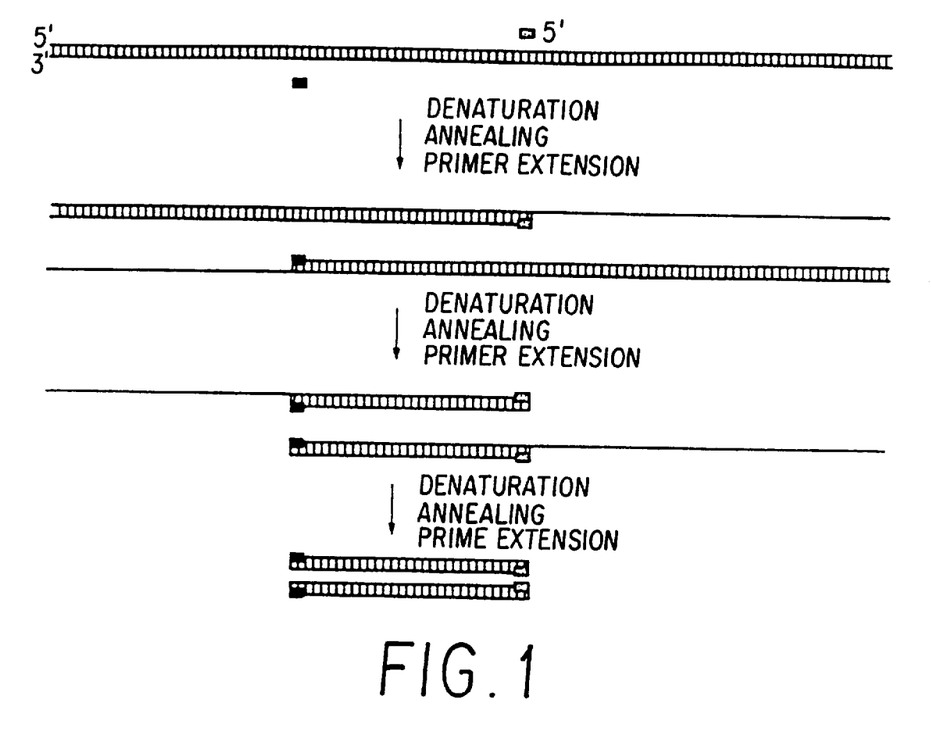
FIG. 1 is a schematic representation of the amplification of a targeted sequence of DNA by PCR. The solid and the stippled block represent the two oligonucleotides bordering the sequence of interest (amplifying primers). The vertical bars represent multiple base pairs. When mixed with denatured DNA and allowed to anneal, these primers will hybridize to their complementary sequences on the DNA. DNA polymerase will then use the DNA as template and the oligonucleotide as primer to synthesize a new strand of DNA. Repeat cycles of denaturation, annealing, and primer extension will yield a pool of amplified target sequence; one such sequence is shown at the bottom.

To circumvent this problem, viral DNA sequences can be amplified using the polymerase chain reaction (PCR) and the products identified by using conventional hybridization techniques for identification of virus type, such as Southern blotting. See C. Oste, *Biotechniques*, 6, 163 (1988) and K. B. Mullis (U.S. Pat. No. 4,683,202). A stretch of nucleotides complementary to the 5' end of a targeted region of the HPV genome and a second stretch complementary to the 3' end of this region are first synthesized. These oligonucleotides are referred to as "primers." When these amplifying primers are allowed to anneal to the total denatured cellular DNA in a clinical sample, they will form duplexes with the single-stranded HPV DNA if it is present. In the presence of a DNA polymerase and a mixture of deoxynucleotide triphosphates, each strand will be elongated as shown in FIG. 1. As this cycle of denaturation, primer annealing and chain extension is repeated, the targeted region of HPV DNA will accumulate exponentially, to about 1 µg of DNA after 30 cycles. This product is easily visible on an agarose gel, thus suggesting the presence of the HPV sequence in the tissue. The diagnosis can be verified by transferring the DNA to nitrocellulose and probing with a probe specific to the HPV type presumed to be present.

Alternatively, one may take advantage of known restriction sites within the HPV DNA to demonstrate that the amplified DNA contains the expected sequence by examining the cleavage pattern(s) generated with one or more restriction endonucleases. Verifying the authenticity of the amplified sequence may be necessary for two reasons: (i) to ensure that sequences complementary to the amplifying primers do not fortuitously happen to be present in cellular DNA which does not contain HPV DNA, and (ii) to verify the HPV type. If the sequences chosen for amplification are conserved among HPV types, then the finding of an amplified product does not implicate a particular HPV type. It should also be possible, based on the binding positions of the two primers, to predict the size of the amplified product. Thus, when that product is found, one can feel reasonably confident that HPV is present. However, two different HPV types may give the same size product, or subtypes of a given HPV may given different size products. Thus, hybridizations should be used to confirm the identity of the amplified sequence until confidence is built that the interpretation of the results is straight-forward. It should be pointed out that, in the absence of "universal" primers, the PCR technique will identify only closely-related, or type-specific sequences, since only a small portion of the genome is analyzed.

The advantages of the PCR technique are that of (i) detection of DNA within a sample can be accomplished without extracting the DNA first, and (ii) the sensitivity is increased by amplifying the DNA present in the lesion. Amplification of HPV DNA sequences by PCR followed by molecular hybridization is the most sensitive technique in that a single molecule or "copy" of HPV DNA can theoretically be detected after appropriate levels of amplification. In practice, the level of sensitivity is about 50–100 copies per sample. The next most sensitive technique is dot blot which can detect about 10,000 molecules while Southern blot can reliably detect about 100,000 copies of DNA.

Nonetheless, PCR has been used for detection of HPV in fresh clinical specimens (L. S. Young et al., *Brit. Med. J.*, 298, 14 (1989)) and has also been adapted for detection of HPV sequences in sections of formalin-fixed, paraffin-embedded cervical intraepithelial neoplasis and invasive cancers. HPV sequences have even been detected in fixed tissues over forty years old (D. Shibata et al., *Cancer Res.*, 48, 4566 (1988)). A distinct disadvantage is the potential for false positive results, due to cross-contamination of specimens or contamination of samples with amplified material.

Virus type-specific primers have been used for amplification of HPV 11, 16 and 18 sequences. (D. Shibata et al., *J. Exp. Med.*, 167, 225 (1988)). However, the ponderous number of primers necessary to amplify DNA from every virus type infecting the anogenital tract makes PCR impractical for diagnosing or for typing HPV in clinical specimens. Also, whether currently untyped HPV strains can be detected by PCR depends on whether or not a universal pair of primers exists which can be used to detect a region conserved among all HPV types. Thus, a need exists for a method to amplify DNA from the large number of HPVs infecting the anogenital tract using only one set of "universal" primers. Identification of a given viral type could then be accomplished by molecular hybridization with oligonucleotide probes complementary to the sequences in the amplified region which are specific for each virus type.

SUMMARY OF THE INVENTION

The present invention is related to two oligonucleotides which function as amplifying primers when used in tandem in the polymerase chain reaction. The two primers, which are identified by the abbreviations IU and IWDO, are of the formulae:

IU: 5'-TIIN$_1$IN$_1$IIN$_2$TAAAACGAAAGT-3' and

IWDO: 5'-N$_1$TCN$_1$N$_3$AIGCCCAN$_2$TGIACCAT-3' wherein N$_1$ is A or G, N$_2$ is C or T and N$_3$ is A or T. The component nucleotides of IU and IWDO are represented by a single-letter code for the corresponding nucleotide bases, wherein A is adenine, C is cytosine, G is guanine, and T is thymine, and wherein I is deoxyinosine-5'-O-phosphate. The deoxyinosine residues can pair with any base, thus stabilizing the duplex. As indicated, the structures of IU and IWDO are to be read from the 5'-hydroxymethyl group on the deoxyribose ring of nucleotide T or N, respectively, to the 3'-hydroxyl group, which is connected to the 5'-hydroxymethyl group on the next nucleoside sugar residue by a phosphate linkage.

Due to the variation permitted at the positions represented by N$_1$, N$_2$ and N$_3$, the preferred embodiments of the present primers are about an equimolar mixture of each of the individual possible oligonucleotides. For example, in practice, IU is prepared and used as an about equimolar mixture of 8 oligonucleotides, each of a fixed sequence, while IWDO is prepared and used as a mixture of 16 oligonucleotides. However, any of these individual oligonucleotides would be expected to be useful by itself as an HPV PRC primer and, in any case, is useful as a component of IU or IWDO. Therefore, every oligonucleotide within the scope of the formulae of IU or IWDO is within the scope of the present invention.

The present "consensus sequence" primers are complementary to DNA sequences in the 5' half of the E1 ORF of HPV and anneal to a wide variety of human and animal papillomavirus DNAs. The present consensus primers have been used for amplification of HPV 6, 11, 16, 18 and 33 DNA, to yield amounts which are detectable by conventional hybridization techniques. In addition, the genomes of both human and animal cutaneous and mucosal viral DNAs whose sequences are unknown have been amplified to detectable quantities using the present primers. Viral genomes in clinical specimens can also be amplified with the present primers, thus providing a general assay for HPV infection.

Thus, used in tandem, primers IU and IWDO provide a method to diagnose for HPV infection in a sample of physiological material comprising:

(a) denaturing the double-stranded HPV DNA in said sample to yield a first single strand and a second single strand of HPV DNA;

(b) reacting said first strand of HPV DNA with a molar excess of the oligodeoxynucleotide primer IU:its complementary region on said first strand and reacting said second strand of HPV DNA with a molar excess of the oligodeoxynucleotide primer IWDO:its complementary region on said second strand under conditions such that each primer anneals to its complementary region and an extension product of each primer is synthesized which is complementary to the strand to which the primer is annealed;

(c) separating the primer extension products from the strands on which they were synthesized to produce single-stranded molecules; and (d) reacting the single-stranded molecules generated from step (c) with the two primers of step (b), in a molar excess of primer:its complementary region, under conditions such that a primer extension product is synthesized using each of the single-stranded molecules as a template.

Preferably, steps (c)–(d) are repeated at least once, most preferably, about 10–50 times to achieve the synthesis of a detectable amount of a DNA sequence corresponding to the double-stranded HPV DNA which overlaps with, and is between the binding sites of the two primers. This synthetic double-stranded HPV DNA then can be labelled, denatured, and assayed for its ability to bind to probes comprising complementary single strands of DNA. Alternatively, unlabelled amplified HPV DNA can be denatured and reacted with labelled probes of known sequence. In each case, hybridization of the probe to the synthetic single-stranded HPV DNA yields a double-stranded PRV DNA molecule comprising a label, the detection of which confirms the presence of HPV in the clinical sample. As used herein, the term "label" includes both a directly detectable label, such as a radioisotope or an enzyme, or an indirectly detectable label, such as a binding site for a detectable label, e.g., an avidin molecule which can bind a biotinylated enzyme. Preferably, the synthetic double-stranded HPV DNA will contain cleavage sites, so that it can be fragmented with one or more restriction endonucleases prior to denaturation. Following denaturation, the fragments can be separated via chromatographic techniques and the individual fragments identified with detectable single-stranded probes of known sequence. Type-specific probes are disclosed, for example, in published European Patent Application No. 301,968 and by A. Cravador et al., in *Molecular and Cellular Probes*, 3, 143 (1989), the disclosures of which are incorporated by reference herein. Of course, such probes can be used with IWDO, in place of IU, to accomplish the type-specific amplification and identification of HPV strains.

In another embodiment, the invention relates to diagnostic kits for the detection of HPV DNA in a sample suspected of being infected with HPV, which kit comprises, in packaged form, a multicontainer unit having (a) one container each of the primers IU and IWDO, wherein each of the primers is substantially complementary to a strand of the HPV DNA such that an extension product synthesized from one primer, when it is separated from its complement, can serve as a template for the synthesis of the extension product of the other primer;

(b) a container containing an agent for polymerization of nucleoside triphosphates;

(c) a container for each of four different nucleoside triphosphates;

(d) a container containing means such as a probe capable of detecting the presence of said DNA in said sample; and, optionally, (e) a container containing means for detecting hybrids of said probe and said sequence.

The present invention also provides a method to synthesize a segment of the HPV genome which corresponds to a portion of the E1 open reading frame (ORF). This DNA fragment can be sequenced to characterize previously unknown HPV types. The synthesis of relatively large amounts of known DNA from this region can be useful to provide material for immunological studies, e.g., for the preparation of subunit vaccines or monoclonal antibodies against HPV. Representative DNA sequences which can be synthesized using IU and IWDO in the PCR are summarized in Table A, below.

TABLE A

Nucleotide Positions for the Primary Annealing Sites of Primers IU and IWDO in the E1 ORF[a] of HPV

| Virus Type | IU | IWDO | Ref. to Sequence Data |
|---|---|---|---|
| HPV1a | 1019 (90)[b] | 1778 (100)[b] | 1 |
| HPV5 | 1180 (86) | 1909 (100) | 2 |
| HPV6b | 1066 (86) | 1912 (100) | 3 |
| HPV8 | 1164 (86) | 1890 (100) | 4 |
| HPV11 | 1166 (86) | 1912 (100) | 5 |
| HPV16 | 1111 (86) | 1942 (100) | 6 |
| HPV18 | 1167 (90) | 2012 (100) | 7 |
| HPV33 | 1122 (77) | 1935 (100) | 8 |

Figure 2A:
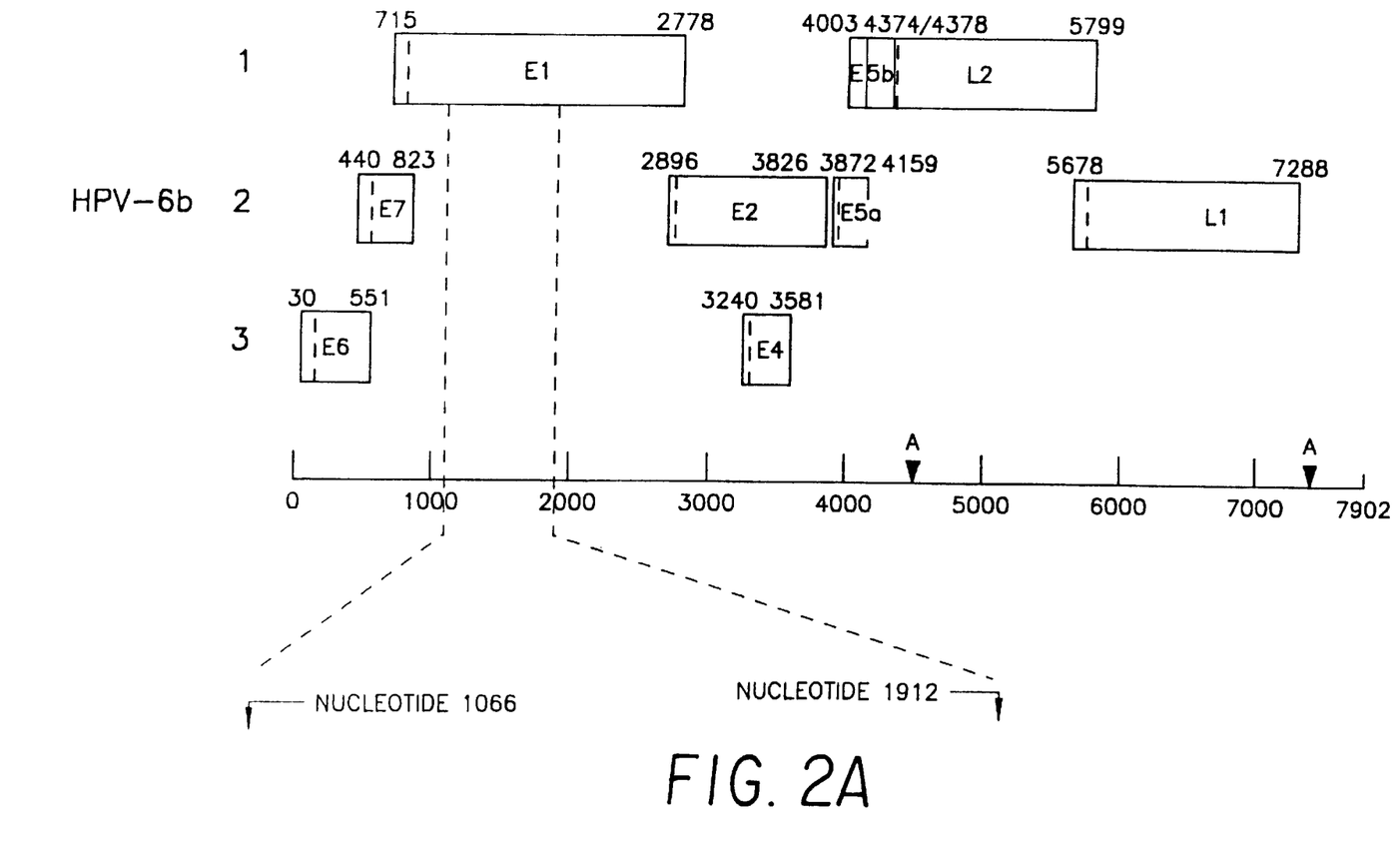
FIG. 2A is a schematic representation of the HPV-6b genome. The symbols "A" on the O-7902 nucleotide scale represent polyadenylation sites. The broken lines in the boxes which represent HPV ORFs indicate the approximate positions of the ATG start codons.
Figure 2B:
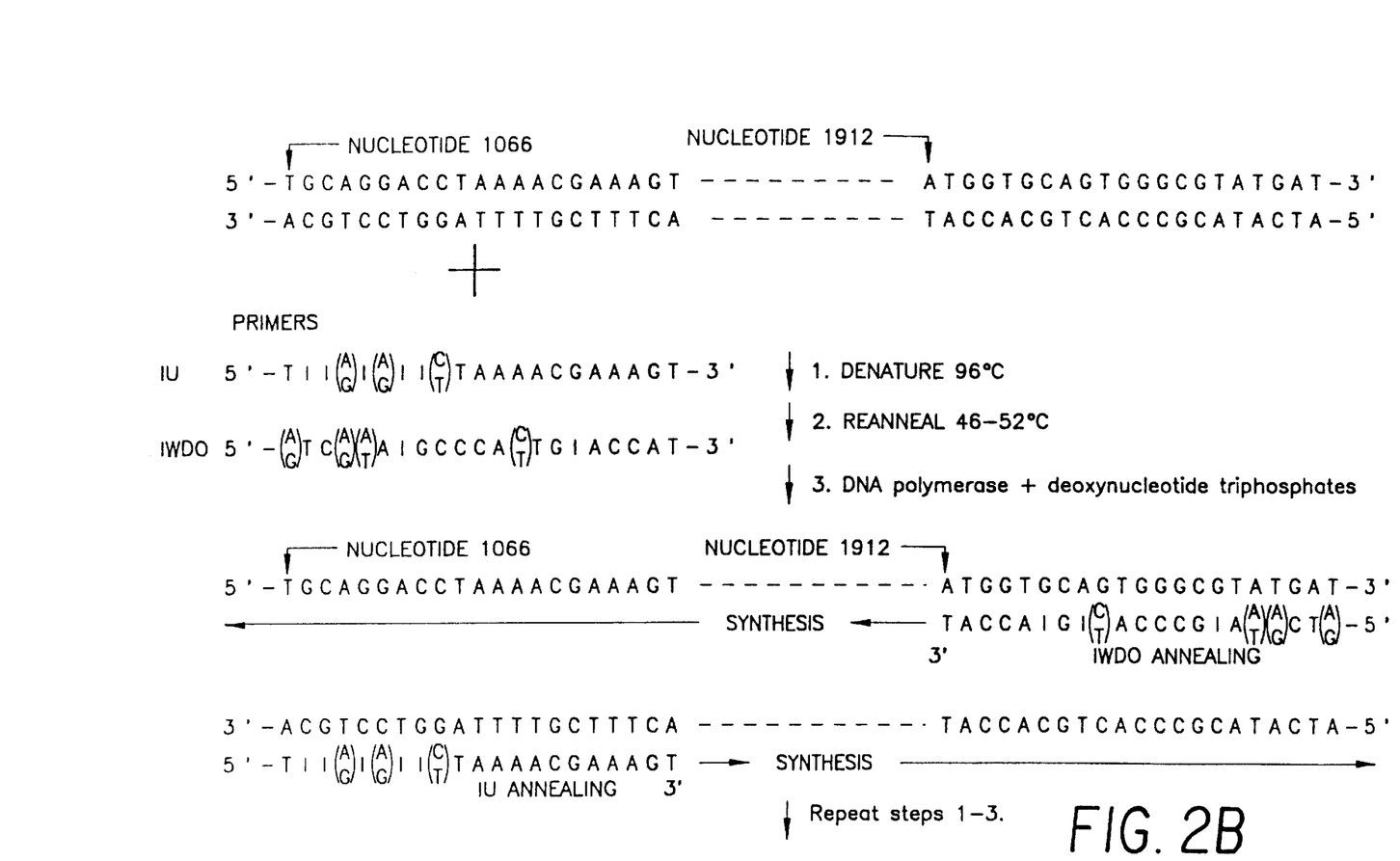
FIG. 2B is a schematic representation of the use of PCR to amplify a DNA sequence in the E1 ORF of HPV using the primers of the present invention.

[a]See FIG. 2. The HPV-6b E1 ORF encompasses nucleotides 715–2278.
[b]Percent homology.
[1]A. L. Chad et al., Virology, 118, 254 (1982); O. Danos et al., EMBO J., 1, 231 (1982).
[2]K. R. Zachow et al., Virology, 158, 251 (1987).
[3]E. Schwarz et al., EMBO J., 2, 2341 (1983).
[4]P. G. Fuchs et al., J. Virol., 58, 626 (1986).
[5]K. Dartman et al., Virology, 151, 124 (1986).
[6]C. C. Baker et al., J. Virol., 61, 962 (1987), A. L. Chad et al., ibid.
[7]S. T. Cole et al., J. Mol. Biol., 193, 599 (1987).
[8]S. T. Cole et al., J. Virol., 58, 991 (1986).

DETAILED DESCRIPTION OF THE INVENTION

In general, the present process uses the PCR to produce, in exponential quantities relative to the number of reaction steps involved, at least one specific HPV DNA sequence. The product of the chain reaction will be a discrete unit of double-stranded DNA with termini corresponding to the ends of the primers employed.

Any source of HPV DNA, in purified or nonpurified form, can be utilized as the starting material for amplification, provided it contains or is suspected of containing HPV DNA.

The oligonucleotide primers may be prepared using any suitable method, such as, for example, the phosphotriester and phosphodiester methods or automated embodiments thereof. In one such automated embodiment, diethylphosphoramidites are used as starting materials and may be synthesized as described by Beaucage et al., *Tetrahedron Letters*, 22, 1859 (1981). One method for synthesizing oligonucleotides on a modified solid support is described in U.S. Pat. No. 4,458,066.

It is necessary to separate the strands of the HPV DNA before they can be used as the templates, either as a separate step or simultaneously with the synthesis of the primer extension products. This strand separation can be accomplished by any suitable method including physical, chemical or enzymatic means. One physical method of separating the strands of the nucleic acid involves heating the nucleic acid until it is completely (>99%) denatured. Typical heat denaturation may involve temperatures ranging from about 80° C. to 105° C., for times ranging from about 1 to 10 minutes. Strand separation may also be induced by an enzyme from the class of enzymes known as helicases or the enzyme RecA, which has helicase activity and, in the presence of riboATP, is known to denature DNA. The reaction conditions suitable for separating the strands of nucleic acids with helicases are described by Cold Spring Harbor Symposia on Quantitative Biology, Vol. XLIII "DNA: Replication and Recombination" (New York: Cold Spring Harbor Laboratory, 1978), B. Kuhn et al., "DNA Helicases", pp. 63–67, and techniques for using RecA are reviewed in C. Radding, *Ann. Rev. Genetics*, 16, 405 (1982).

The PCR can be performed using any suitable method. Generally, it is carried out in a buffered aqueous solution, preferably at a pH of 7–9, most preferably about 8. Preferably, a molar excess (for cloned DNA, usually about 1000:1 primer:template, and for genomic nucleic acid, usually about $10^6$:1 primer:template) of the two oligonucleotide primers is added to the buffer containing the separated HPV DNA strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of its complementary strand (template) when the sequence to be amplified is contained in a complex mixture of long-chain nucleic acid strands. A large molar excess is preferred to improve the efficiency of the process.

The deoxyribonucleoside triphosphates dATP, dCTP, dGTP, and TTP are also added to the synthesis mixture in adequate amounts and the resulting solution is heated to about 90° C.–100° C. for from about 1 to 10 minutes, preferably from 1 to 4 minutes. After this heating period, the solution is allowed to cool and primer hybridization is carried out at about 35° C.–55° C. To the cooled mixture is added an appropriate agent for inducing or catalyzing the primer extension reaction, and the reaction is allowed to occur under conditions known in the art. This synthesis reaction may occur at from room temperature up to a temperature above which the inducing agent no longer functions efficiently. Thus, for example, if Taq DNA polymerase is used as inducing agent, the temperature is generally about 50° C.–75° C.

The inducing agent may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, and other available DNA polymerases such as the thermostable DNA polymerase purified from Thermus aguaticus(Taq DNA polymerase). The use of Taq DNA polymerase is preferable, since the addition of fresh enzyme after each thermal denaturation step is not required. Generally, the synthesis will be initiated at the 3' end of each primer and proceed in the 5' direction along the template strand, until synthesis terminates, producing molecules of different lengths. Each newly synthesized strand and its complementary nucleic acid strand form a double-stranded molecule which is used in the succeeding steps of the process. In the next step, the strands of the two double-stranded molecules are separated to provide four single-stranded molecules.

New nucleic acid is synthesized on the single-stranded molecules. Additional inducing agent, nucleotides and primers may be added if necessary for the reaction to proceed under the conditions prescribed above. Again, the synthesis will be initiated at one end of the oligonucleotide primers and will proceed along the single strands of the template to produce additional nucleic acid. After this step, half of the extension product will consist of the specific nucleic acid sequence bounded by the two primers. The steps of this process can be repeated indefinitely, being limited only by the amount of primers, inducing agent and nucleotides present. The amount of original nucleic acid remains constant in the entire process, because it is not replicated. The amount of the long products increases linearly because they are produced only from the original nucleic acid. The amount of the specific sequence increases exponentially. Thus, the specific sequence will become the predominant species.

The present invention can be performed in a step-wise fashion where, after each step, new reagents are added, or simultaneously, where all reagents are added at the initial step, or partially step-wise and partially simultaneous, where fresh reagent is added after a given number of steps. If a method of strand separation, such as heat, is employed which will inactivate the inducing agent, as in the case of a heat-labile enzyme, then it is necessary to replenish the inducing agent after every strand separation step. The simultaneous method may be utilized when an enzymatic means is used for the strand separation step. In the simultaneous procedure, the reaction mixture may contain, in addition to the nucleic acid strand(s) containing the desired sequence, the strand-separating enzyme (e.g., helicase), an appropriate energy source for the strand-separating enzyme, such as rATP, the five nucleotides, the oligonucleotide primers in molar excess, and the inducing agent, e.g., Klenow fragment of E. coli DNA polymerase I. If heat is used for denaturation in a simultaneous process, a heat-stable inducing agent such as Taq DNA polymerase may be employed which will operate at an elevated temperature, preferably 65° C.–90° C., depending on the inducing agent, at which temperature the DNA will consist of single and double strands in equilibrium. The upper temperature will depend on the temperature at which the enzyme will degrade or the temperature above which an insufficient level of primer hybridization will occur. Each step of the process will occur sequentially not-withstanding the initial presence of all the reagents. Additional materials may be added as necessary. After the appropriate length of time has passed to produce the desired amount of the specific nucleic acid sequence, the reaction may be halted by inactivating the enzymes in any known manner or separating the components of the reaction. The process of the present invention may be conducted continuously. In one embodiment of an automated process, the reaction may be cycled through a denaturing region, a reagent addition region, and a reaction region.

A rapid means for synthesizing fluorescent derivatives of oligonucleotides has been developed. This method offers an additional nonradioactive means of detecting specific DNA fragments. Synthetic copies of a portion of each gene-specific probe are synthesized and fluorescently derivatized. Different dye-oligonucleotide conjugates would be synthesized for each HPV subtype, each with separate spectral properties. These fluorescent probes would be used in a manner identical to that described for the radioactive probes and hybridization detected by fluorometry. However, a mixture of probes could be employed.to probe a single DNA fragment mixture, since hybridization of each probe can be visualized by a band of fluorescence at a discrete wavelength.

For use as a probe in DNA:DNA hybridization analysis, the labelled DNA is denatured, i.e., made into single-stranded DNA, as by exposure to elevated temperatures in an aqueous medium. The resultant single-stranded DNA is brought into contact with denatured DNA fragments derived from the PCR reaction mixture. The labelled probe will hybridize, or bind, only to DNA strands comprising complementary base pair sequences, thus identifying DNA fragments derived from HPV.

A number of experimental techniques have been developed to assay mixtures of genomic DNA fragments with radiolabelled DNA probes. A preferred assay has been disclosed by E. M. Southern, in *J. Mol. Biol.*, 98, 503 (1975). In "Southern blotting," the DNA fragments to be screened are transferred from an agarose gel to a solid support such as a nitrocellulose or nylon membrane. The membrane permits the bound DNA to be analyzed by DNA:DNA or DNA:RNA hybridization methods. In a first step, the fragments generated by digestion of genomic DNA by one or more restriction endonucleases are separated chromatographically in an agarose gel by electrophoresis according to their size. The fragments in the gel are treated at room temperature in aqueous acid, and are then denatured under basic conditions. Finally, the gel is neutralized and placed on top of buffer-saturated filter paper. The ends of the filter paper extend into a reservoir containing the buffer. The top surface of the gel is covered with the membrane onto which the DNA is to be absorbed, or "blotted." The membrane is then overlaid with dry filter paper and a stack of dry absorbent paper towels. A weight is placed on the stack of paper to ensure even contact between the membrane and gel. Buffer carrying the single-stranded DNA is absorbed by the dry paper as it passes up through the gel. The DNA then binds to the membrane. The blotting procedure usually takes from about 4 to 16 hours to transfer all of the DNA from the gel to the membrane. After transfer, the membrane is heated to firmly attach the DNA to the membrane. Solutions containing radiolabelled probes can then be brought into contact with the genomic DNA fragments fixed to the membrane. Any hybridization is detected by autoradiography, e.g., by exposing the membrane to x-ray film.

The presence or absence of the target HPV DNA sequence can be determined via the use of single-stranded labelled HPV DNA probes of known sequence. These probes can be derived by excising portions of the E1 ORF from known recombinant plasmid vectors comprising portions of the HPV genome.

To complete the synthesis of the present probes, detectable labels are introduced, e.g., a radiolabel or fluorescent molecule. For example, probes can be made radioactive using the method of nick-translation. Singlestrand breaks, or "nicks," are introduced at widely separated intervals in double-stranded DNA by limited digestion with the enzyme DNase I. At each break, DNA polymerase I of *E. coli* is used to 1) incorporate radiolabelled nucleotides at a free 3'-OH group, and 2) extend the nick along the DNA duplex by the 5'-3' exonucleolytic activity of polymerase I. The end result is a double-stranded DNA molecule which incorporates radiolabelled nucleotides randomly into each strand.

The strong and specific association between biotin (vitamin H) and the egg-white glycoprotein avidin can provide the basis for a non-radioactive means of detecting DNA:DNA hybridization. See Ward, European Patent No. 63,879. The enzymatic incorporation by nick-translation of biotinylated nucleotides into double-stranded DNA has been disclosed. The biotinylated DNA is then used to probe target DNA fragments in a manner similar to the use of radiolabelled probes. Specific DNA:DNA hybridization is then detected by soaking the blot in a solution containing the avidin protein. Avidin binds to the DNA:DNA complexes via the biotin group on the DNA probe. The avidin:biotin:DNA complexes are detected utilizing an indicator enzyme attached to the avidin protein. This enzyme catalyzes the formation of a precipitate which permits the visualization of the DNA:DNA complex as a band of colored material. For example, see U.S. Pat. No. 4,228,237, the disclosure of which is incorporated by reference herein. The amplification process can also be utilized to produce sufficient quantities of DNA such that detection by a simple non-specific DNA stain as ethidium bromide can be employed so as to make a DNA diagnosis directly.

In addition to detecting HPV in the genome of organisms, the process herein can also be used to detect DNA polymorphism which may not be associated with any recognized pathological state associated with HPV.

The invention will be further described by reference to the following detailed Examples.

EXAMPLE I

Diagnosis of HPV by PCR

A. Preparation of Clinical Samples

Cervical, vulvar or penile scrape or swab specimens were collected from individuals likely to have genital HPV infections and were suspended in phosphate-buffered saline (PBS). The total cellular DNA was purified by lysing the cells in 0.6% sodium dodecyl sulfate and 0.01M EDTA containing 100 µg/ml proteinase K. Samples were incubated for 18 hrs at 37° C. Proteins were removed by two extractions with phenol followed by two chloroform:isoamyl alcohol (24:1 v/v) extractions. Nucleic acids were precipitated with ethanol. RNA was removed by treatment with RNase followed by Proteinase K digestion and phenol and chloroform extractions as above. DNA was precipitated with ethanol, resuspended in $H_2O$ and digested with BamHI and HindIII by the procedure of W. D. Lancaster et al., in *The Human Oncogenic Viruses*, A. A. Luderer et al., eds., Humana Press, Clifton, NJ (1986) at pages 153–183. Approximately 0.01–0.1 µg of DNA was used in the PCR.

B. Preparation of Known HPV DNA Sequences

HPV sequences in known plasmids were released from flanking vector sequences by cleavage at the unique restriction enzyme site of insertion. All of the cleavage sites were outside of the E1 ORF. The plasmid sources of the HPV sequences are given in Table B, below.

TABLE B

HPV Plasmids

| HPV Type | Literature Reference |
|---|---|
| 2b | C. A. Heilman et al., J. Virol., 36, 395 (1980). |
| 4 | C. A. Heilman et al., J. Virol., 36, 395 (1980). |
| 6 | E. M. DeVilliers et al., J. Virol., 40, 932 (1981). |
| 11 | L. Grissman et al., J. Virol., 44, 393 (1982). |
| 16 | M. Durst et al., PNAS USA, 80, 3812 (1983). |
| 18 | M. Boshart et al., EMBO J., 3, 1151 (1984). |
| 31 | A. T. Lorincz et al., J. Virol., 58, 225 (1986). |
| 33 | S. Beaudenon et al., Nature, 321, 246 (1986). |
| 35 | A. T. Lorincz et al., Virology, 159, 187 (1987). |
| 52 | K. Shimoda et al., J. Gen. Virol., 69, 2925 (1988). |

C. Primers

The primers IU and IWDO were synthesized on a DNA synthesizer (model 380, Applied Biosystems Inc., Foster City, CA), in accord with the general synthetic methodology of M. D. Matteucci et al., *Tetrahedron Letters*, 21, 719 (1980) as improved by L. J. McBride et al., *Tetrahedron Letters*, 24, 245 (1983). Briefly, a first 2'-deoxynucleoside is linked to a solid support such as carboxylated silica gel or porous glass beads by forming an ester linkage between the 3'-OH group of the nucleoside and a carboxylic acid group attached to the support, wherein the 5'-OH group of the nucleoside is protected, e.g., with a dimethoxytrityl moiety. This reaction can be carried out in pyridine using dicyclohexylcarbodiimide as a condensing agent. Following blocking of the residual carboxyl groups on the support, the 5'-OH protecting group is cleaved and the OH group of the immobilized nucleoside is reacted with a phosphomorochloridite nucleoside prepared by reacting a 5'-O-protected nucleoside with methyl phosphorodichloridite in the presence of base at low temperature. Alternatively, the chloro-leaving group of the phosphomorochloridite can be replaced by the moiety—$NH^-(iPr)_2$ by reaction of protected nucleoside with a phosphoramidite in the presence of base, and the coupling reaction carried out using weak acid. The resultant immobilized dinucleoside phosphite is oxidized to the phosphate, e.g., using iodine in a mixture of water/lutidine/THF. The POMe group is cleaved with thiophenoxide to yield the phosphate linkage, the base amino groups are deprotected and the finished oligonucleotide is cleaved from the support, e.g., with dilute base.

The individual oligonucleotides which make up IU and IWDO can be synthesized separately and combined, or mixtures protected of two phosphomonochloriditite nucleosides can be added at the appropriate steps in the synthesis of either primer. See also, M. H. Caruthers et al. (U.S. Pat. No. 4,458,066) for a detailed description of this synthetic route. The primers comprise 21 nucleoside residues of the following sequences:

IU: 5'-TII(AG)I(AG)II(CT)TAAAACGAAAGT-3' and
IWDO: 5'-(AG)TC(AG)(AT)AIGCCCA(CT)TGIACCAT-3'

Deoxyinosine (I) residues are used in place of four base (A, C, T, G) permutations to facilitate stabilization during annealing (E. Ohtsuka et al., *J. Biol. Chem.*, 260, 2605 (1985)). The binding sites of these primers on sequenced HPV genomes are given in Table A.

D. Polymerase Chain Reaction (PCR)

PCR for amplification of DNA sequences was carried out as described by Saiki et al., *Science*, 230, 1350 (1985), and as summarized on FIG. 2. Briefly, amplification reactions were performed in a volume of 100 µl in 0.5 ml microcentrifuge tubes in 10 mM Tris-HCl, pH 8.3, 1.5 mM $MgCl_2$, 50 mM KCl with the deoxyribonucleotides (dATP, dGTP, dCTP, TTP) at a final concentration of 200 µM each and primers at 1 µM each. HPV DNAs at a concentration of 1 ng in 100 µl of the amplificiation mixture were denatured at 95° C. for 5 min before the addition of 2.5 U *Taq* DNA polymerase (Perkin-Elmer, Cetus). (H. A. Erlich et al., *Nature*, 331, 461 (1988)). The amplification mixture was overlayed with 100 µl of mineral oil and the amplifications carried out in a DNA thermal cycler (Perkin-Elmer, Cetus). DNAs were annealed at 37° C. for 2 min with a rise in temperature to 55° C. over a period of 90 sec. The first extension was at 55° C. for 1 min followed by a rise in temperature to 72° C. in 40–60 sec with a 3 min extension period. DNAs were denatured at 94° C. and the steps repeated for an additional 24 cycles unless specified otherwise.

E. Labelling HPV DNA

PCR products derived from recombinant HPV DNA templates were electrophoresed in low melting agarose gels. Ethidium bromide-stained 850 bp fragments, which were the approximate molecular weight of the expected amplification products, were excised and labelled with alpha-$^{32}$P-dATP by the random primer technique using Klenow polymerase directly within the low melting agarose (A. P. Feinberg et al., *Anal. Biochem.*, 132, 6 (1983)). Specific activities of about $10^8$ counts/min/µg DNA were routinely obtained with this method. The labelled PCR products were hybridized to Pst I digests of the known HPV DNAs under stringent conditions.

F. Results

Based on the guanine+cytosine (G+C) content and the size of the universal primers IWDO and IU, the calculated temperature of dissociation (Td) for the two primers was 58° C. and 48° C., respectively. (B. D. Hames et al., *Nucleic Acid Hybridization—A Practical Approach*, IRL Press, Oxford, England (1985)). Annealing of these primers was carried out at 11° C. below the temperature of dissociation (Td) of IU.

In preliminary studies, it was found that the amplification reactions failed to yield a detectable product when carried out at the optimal temperature of *Taq* polymerase (72° C.). Presumably, one or both primers dissociated from the template before extension was initiated. To maintain annealing of primers to the template, the reaction temperature was slowly increased from 37° C. to 55° C. for the first period of polymerization (1 min) followed by a second period of extension at 72° C. for 3 min. All HPV DNAs amplified under these conditions contained the expected 850 nucleotide fragment. In addition to the expected band, HPV18 consistently showed the presence of a fragment about 550 nucleotides in length.

To determine the source of this additional fragment, PCR was carried out using only one of the two primers. When IWDO was used as the primer, HPV6 and HPV18 DNAs showed fragments of about 850 and 550 nucleotides, respectively. No amplification was observed with HPV11, HPV16, or HPV33 DNAs when IWDO was used as the sole primer. When IU was used as primer, a very faint band at about 850 bp was detected only for HPV 33. The extra fragments for HPV 6 and HPV 33 observed after single primer amplification were not detected in dual primer reactions because of coigration with the expected 850 bp fragment.

Examination of the viral sequences revealed potential alternative annealing sites at 69% homology with IWDO only for HPV 6 and HPV 18. This degree of mismatch would be tolerated under the conditions of primer annealing (37° C.). The annealing (target) site for IWDO on HPV 18 DNA is at position 2012 on the coding (positive) strand. A potential alternative binding site for IWDO in the correct orientation for amplification was detected on the negative strand 545 base pairs (bp) upstream of the target site. Other annealing sites were also localized but only one additional set was properly oriented to permit amplification. One site was at position 3783 on the positive strand and the other site 575 nucleotides downstream on the negative strand. For HPV 6, only one set of additional alternative annealing sites were detected. One site was located at position 3006 on the positive strand and the other 859 bp downstream on the negative strand. For HPV 33, the target site for IU was at position 1122 on the coding strand; however, no alternative binding sites in the correct orientation that would yield a fragment of about 850 bp was detected on the non-coding strand. However, a set of alternative binding sites were located at position 976 on the positive strand and 845 bp downstream in the correct orientation on the negative strand.

To eliminate any alternative primer binding sites, the temperature of annealing was increased. The PCR was repeated for HPV 6, 18 and 33 using only one primer and the annealing temperature increased from 37° C. to 46° C. HPV 6 and 33 did not show amplification at this temperature but a 550 bp band was still present for HPV 18. When the temperature of annealing was increased from 46° C. to 52° C., HPV 18 failed to amplify using a single primer. At an annealing temperature of 52° C., no extension time was included at that temperature but rather, a slow increase in temperature from 52° C. to 72° C. over a period of 90 sec followed by extension completed the cycle. By increasing the temperature to 52° C., the annealing of IU or IWDO to secondary sites was prevented. This was confirmed by the disappearance of these additional bands in HPV 6, 18 and 33. Amplification using these two primers was successful even though annealing was carried out at a temperature 4° C. higher than the lowest Td for IU.

No differences were noted in the intensity of ethidium bromide stained fragments generated at annealing temperatures of 46° C. versus 52° C. However, serial dilution of the HPV 6 template indicated about two orders of magnitude difference in the amount of DNA amplified at limiting amounts of template. At 46° C., 0.01 pg of amplified fragment could be detected whereas only 1.0 pg was detectable at 52° C. after 40 cycles of amplification. Hybridization revealed that the product of amplification could be detected from as little as 0.001 fg (1–10 molecules) of HPV 6 DNA at 46° C., and 1 pg or $2\times10^5$ molecules at 52° C.

To evaluate the utility of the primers as HPV consensus primers, the amplification of a variety of human and animal papillomavirus DNAs whose sequences are not available was attempted. Cloned HPV 2, 4, 31, 35 and 52 as well as bovine papillomavirus type 7 (BPV 7) and canine oral papillomavirus (CO PV) DNA sequences were tested. At a temperature of annealing of 52° C., amplification of all of these DNAs, except for BPV 7, produced fragments about 850 bp in length. Although equal amounts (1 ng) of viral DNA was used for amplification, HPV 2 produced a detectable but fainter signal suggesting that one or both primers did not efficiently anneal to the template.

Amplified fragments were labelled and hybridized to PstI digests of the known HPV DNAs under standard (Tm-25) conditions. In each instance, the PCR product of each HPV hybridized only to its respectively template DNA. Furthermore, only the fragment containing the target sites for the primers hybridized to the PCR product (see Table A). Thus, a PCR product was produced that was specific for virus type as well as the predicted region of viral DNA.

EXAMPLE 2

Amplification of PRV DNA from Clinical Samples

DNA from clinical samples, previously typed by Southern blot hybridization, were selected to be amplified using these universal primers. After double digestion with BamHI and HindIII, the samples were subjected to 25 cycles of amplification in the presence of IU and IWDO as well as B-globin primers at an annealing temperature of 46° C. Aliquots (15 µl) of the amplification mixture was electrophoresed through 0.8% agarose gels, transferred to nylon membranes and hybridized to labelled amplified fragments of HPV 6, 11, 16, 18 or 31 as well as B-globin oligomer under standard (Tm-25° C.) conditions. For negative controls, three samples previously negative by Southern blot were used as well as 1 µg DNA from the human cell line 293.

All samples hybridized to a B-globin probe indicating sufficient cellular DNA was present in the sample and that the amplification reaction was not inhibited. The HPV hybridization results on the amplified DNA correlated with those of previous Southern blots. Two of the previously negative samples by Southern blot were faintly positive for HPV 31. These samples represented a biopsy of normal vulva and squamous cell carcinoma of the cervix. The positive normal vulva could be the result of latent infection and the squamous cell cervical cancer could have been negative by Southern blot because of low virus DNA concentration. Alternatively, these two samples could have been contaminated during the numerous manipulations involved in DNA extraction, restriction enzyme digestion and PCR. This seems unlikely, however, since the other negative control (normal cervix) and DNA from human cell line 293 remained negative. Furthermore, in no instance was HPV DNA detected from two different types in any sample.

The above results confirm that IU and IWDO can be used in combination as universal primers for amplification of HPVs associated with genital tract infections. The primers of the present invention are "universal" in the sense that they obviate the need for type-specific primers in the PCR.

Because these primers show varying degrees of homology with the templates, an annealing temperature was often employed which was based on the lowest possible Td. Amplification at this temperature resulted in unexpected bands that were eliminated by raising the annealing temperature. However, this temperature increase resulted in a two-fold order reduction in efficiency of amplification. This could be accounted for by the degeneracy of the primers in which only a small proportion of the total primer formed thermostable duplexes with the template. Deoxyinosine was used in the place of a possible four base redundancy to increase the thermal stability of the primers. This has the additional advantage of avoiding the reduction in the concentration of the primers when there are degenerate positions. Amplification of normal cellular DNA with the universal primers at low annealing temperatures failed to generate DNA fragments which hybridized to HPV probes.

Although it was expected that the consensus primers of this invention would be effective for amplification of HPV 6, 11, 16, 18 and 33 DNA, since these sequences were known, a number of unsequenced HPV DNAs could be amplified, which were derived from a variety of tissue sources. Since the universal primers anneal to sequences which are highly conserved among the tested HPVs, these sequences are likely to be sequences which are characteristic of the entire virus genus. Therefore, the universal primers described here can be used for the detection of as yet uncharacterized virus types. They can also be used for the confirmation of HPV in lesions not normally associated with HPV infection. This broad utility may be limited to HPVs since BPV 7 DNA could not be amplified even though COPV DNA was amplified. IU showed little homology to the BPV-1 and COPV sequences whereas IWDO had a high degree of homology. This indicated that annealing sites were present for only one of the two primers.

Since benign and premalignant lesions contain episomal HPV DNA sequences, PCR using these universal primers can be useful as a general screening for detection of viral sequences in clinical specimens. The resultant amplified fragments could then be typed with specific oligonucleotide probes.

The invention has been described with reference to various specific and preferred embodiments and techniques. However, it should be understood that many variations and modifications may be made while remaining within the spirit and scope of the invention. All cited patents, published papers and other documents cited herein are incorporated by reference as though fully set forth herein.

What is claimed is:

1. A method of detecting human papillomavirus (HPV) in a sample of a physiological material infected with HPV comprising:

(a) separating double-stranded DNA from the E1 open reading frame of HPV in said sample to yield a first single strand of HPV DNA and a second single strand of HPV DNA;

(b) reacting said first single strand of HPV DNA with a molar excess of the oligodeoxynucleotide primer 5'-TIIN$_1$IN$_1$IIN$_2$TAAAACGAAAGT-3' wherein N$_1$ is A or G, and N$_2$ is C or T;
and reacting said second strand of HPV DNA with a molar excess of the oligodeoxynucleotide primer 5'-N$_1$TCN$_1$N$_3$AIGCCCANTGIACCAT-3' wherein N$_1$ and N$_2$ are defined as above, and N$_3$ is A or T; under conditions such that each primer anneals to its complementary region and an extension product of each primer is synthesized which is complementary to the strand to which the primer is annealed;

(c) separating the primer extension products from the strands on which they were synthesized to produce four single-stranded molecules;

(d) reacting the four single-stranded molecules generated from step (c) with the two primers of step (b) in a molar excess of primer under conditions such that each primer anneals to its complementary region and an extension product of each primer is synthesized using each of the single-stranded molecules as templates; and (e) repeating steps (c)-(d) to accumulate a detectable amount of double-stranded DNA corresponding to the HPV DNA between the HPV DNA sequences complementary to the DNA sequences of the oligodeoxynucleotide primers; and (f) detecting said detectable amount of DNA.

2. The method of claim 1 wherein the detectable amount is detected by denaturing it to yield two single-strands of HPV DNA, annealing at least one of said single strands to a labelled oligonucleotide probe, and detecting said label.

3. The method of claim 2 wherein the labelled oligonucleotide probe comprises a radiolabel.

4. The method of claim 2 wherein the labelled oligonucleotide probe is labelled with a binding site for a detectable label.

5. The method of claim 1 wherein the detectable amount is detected by binding a detectable label thereto and detecting said label.

6. The method of claim 1 wherein steps (c)-(d) are repeated about 10-50 times.

7. The method of claim 1 wherein the separation in step (a) and in step (c) is accomplished by thermally denaturing the double stranded DNA.

8. The method of claim 7 wherein the denaturation step is carried out at about 95° C.–97.5° C.

9. The method of claim 1 wherein the annealing in steps (b) and (d) is carried out at about 35° C.–55° C.

10. The method of claim 1 wherein steps (b) and (d) are accomplished by treatment with four different nucleoside triphosphates and an agent for polymerization, which are added together with or separately from said primers.

11. The method of claim 10 wherein the agent for polymerization is Taq polymerase.

12. The method of claim 11 wherein the synthesis in steps (b) and (d) is carried out at about 50° C.–75° C.

13. An oligonucleotide of the formula:

5'-$N_1$TC$N_1$$N_3$AIGCCCA$N_2$TGIACCAT-3' wherein $N_1$ is A or G, $N_2$ is C or T and $N_3$ is A or T;

or its complementary sequence wherin the complementary base of I is I in said complementary sequence.

* * * * *